(12) United States Patent
Farquharson et al.

(10) Patent No.: US 8,932,524 B2
(45) Date of Patent: Jan. 13, 2015

(54) APPARATUS FOR EFFECTING ANALYSIS WITH RAPID ANALYTE CHEMICAL SEPARATION AND SUBSEQUENT DETECTION

(75) Inventors: Stuart Farquharson, Meriden, CT (US); Paul Maksymiuk, Albuquerque, NM (US); Chetan S. Shende, Vernon, CT (US)

(73) Assignee: Real-Time Analyzers, Inc., Middletown, CT (US)

( * ) Notice: Subject to any disclaimer, the term of this patent is extended or adjusted under 35 U.S.C. 154(b) by 794 days.

(21) Appl. No.: 13/199,601

(22) Filed: Sep. 2, 2011

(65) Prior Publication Data

US 2011/0317159 A1 Dec. 29, 2011

Related U.S. Application Data

(60) Division of application No. 12/322,158, filed on Jan. 29, 2009, now Pat. No. 8,012,763, which is a continuation-in-part of application No. 10/818,201, filed on Apr. 5, 2004, now abandoned, which is a continuation-in-part of application No. 10/372,622, filed on Feb. 21, 2003, now Pat. No. 6,943,032.

(51) Int. Cl.

| | | |
|---|---|---|
| *G01N 21/00* | (2006.01) | |
| *G01N 21/65* | (2006.01) | |
| *G01N 1/40* | (2006.01) | |
| *G01N 30/74* | (2006.01) | |
| *B01L 3/00* | (2006.01) | |
| *G01N 30/60* | (2006.01) | |
| *G01N 30/78* | (2006.01) | |

(52) U.S. Cl.
CPC .............. *G01N 21/658* (2013.01); *G01N 1/40* (2013.01); *G01N 30/74* (2013.01); *B01L 3/5027* (2013.01); *G01N 30/6082* (2013.01); *G01N 30/6095* (2013.01); *G01N 30/78* (2013.01)
USPC ........................................ 422/82.05; 422/70

(58) Field of Classification Search
CPC ...... G01N 21/658; G01N 21/65; G01N 30/02; G01N 2021/656; G01N 2021/655; G01N 27/44721; G01N 33/587; G01N 33/53; G01N 33/552; G01N 33/553; G01N 33/543; G01N 15/1434; G01N 15/147; G01N 15/1484; G01N 1/24; G01N 1/40; G01N 27/44791; G01N 30/90; G01N 2610/00; C12Q 2547/101; B01J 2219/00702; B01J 2219/0059; B01J 2219/005; B01J 2219/00
See application file for complete search history.

(56) References Cited

PUBLICATIONS

Cabalin et al. "Fast spatially resolved surface-enhanced Raman spectrometry on a silver coated filter paper using charge-coupled device detection", Anal. Chim. Acta, 1995, v. 310, pp. 337-345.*
Nirode et al. "On-Column Surface-Enhanced Raman Spectroscopy Detection in Capillary Electrophoresis Using Running Buffers Containing Silver Colloidal Solutions", Anal. Chem. 2000, v. 72, pp. 1866-1871.*

* cited by examiner

*Primary Examiner* — Yelena G Gakh
(74) *Attorney, Agent, or Firm* — Ira S. Dorman

(57) ABSTRACT

A stationary medium is employed both to separate chemicals from a sample solution and also to generate surface-enhanced Raman scattering, so that spectral analysis of the separated analyte chemical can be performed. Applied driving force causes the sample to flow into the stationary medium and to distribute therethrough, thereby causing rapid separation of the analyte chemical, and surface-enhanced Raman scattered radiation is quickly detected, at a plurality of locations along a flow path defined by the stationary medium, for ultimate analysis.

20 Claims, 7 Drawing Sheets

APPARATUS FOR EFFECTING ANALYSIS WITH RAPID ANALYTE CHEMICAL SEPARATION AND SUBSEQUENT DETECTION

CROSS-REFERENCE TO RELATED APPLICATIONS

The application is a divisional of U.S. patent application Ser. No. 12/332,145, filed Jan. 29, 2009 now U.S. Pat. No. 8,012,763, which is a continuation-in-part of U.S. patent application Ser. No. 10/818,201 filed Apr. 5, 2004 now abandoned, which in turn is a continuation-in-part of U.S. patent application Ser. No. 10/372,622, filed Feb. 21, 2003 now U.S. Pat. No. 6,943,032.

STATEMENT REGARDING FEDERALLY SPONSORED RESEARCH OR DEVELOPMENT

The United States Government has rights in this invention pursuant to National Science Foundation Contract No. DMI-0060258.

BACKGROUND OF THE INVENTION

The combination of chemical separation and detection has long been recognized as invaluable to the analytical chemist in identifying chemicals at extremely low concentrations. One of the most successful combinations employs gas chromatography for separation and infrared spectroscopy for detection (P. R. Griffiths, J. A. De Haseth, *Fourier Transform Infrared Spectrometry*, Wiley InterScience, 481 (2007), ISBN 0470106298).

Recently, the combination of chromatography with surface-enhanced Raman spectroscopy (SERS) has been investigated to analyze trace chemicals in solution, at part-per-billion concentrations. Known advantages provided by SERS include high chemical specificity through abundant molecular vibrational information (similar to infrared spectroscopy), and extreme sensitivity, as demonstrated by the detection of single molecules. (See K. Kneipp, Y. Wang, R. R. Dasari and M. S. Feld, Appl. Spectrosc., 49, 780 (1995); and S. Nie and S. R. Emory, Science, 275, 1102 (1997)).

Initially, thin layer chromatography (TLC) was investigated with SERS. In one example, the TLC plates were used to first separate the analytes, were then coated with a silver colloid to generate SERS, and finally were employed to make measurements using a Raman spectrometer (J-M. L. Sequaris and E. Koglin, Anal. Chem., 59, 525 (1987)); the entire analysis took from 30 to 60 minutes. In a second example, the TLC plates were coated with silver prior to attempted separation but, as the authors conclude (N. J. Szabo and I. D. Wineford-ner, Appl. Spectrosc., 51, 965 (1997), separation required 40 to 45 minutes, SERS activity was poor, and "Neither material [TLC plates] was found to be suitable for this application [i.e., TLC plus SERS]." In a similar example (L. M. Cabalin and J. J. Laserna, Anal. Chim. Acta, 310, 337 (1995)), silver-coated filter paper was used to detect analytes by SERS. The analyte was added dropwise (spotted) onto the paper and dried; additional drops of analyte were added to the spot and dried, multiple times, and then the spot was measured using a two-dimensional detector.

To a large extent, liquid chromatography has replaced TLC for chemical separations, primarily because it is more efficient for separating chemicals. Separation efficiency, defined as the ability to spatially resolve chemicals in a relatively short period of time, typically 20 to 30 minutes, can be quantified in terms of the number of theoretical plates a column provides (L. S. Ettre, "Nomenclature For Chromatography", Pure & Appl. Chem., 65, 819 (sp. p. 484) (1993)). The idea is that the column contains a number of separate hypothetical zones, stages or layers (i.e. theoretical plates), and that the analyte comes to equilibrium between the stationary phase and the mobile phase at each layer as the mobile phase moves down the column. Knowing the retention time, $t_R$, and the width at half height, $W_{1/2}$, for the peak of an eluted analyte, the theoretical number of plates, $N_{eff}$ can be determined for a conventional chromatography column according to the expression:

$$N_{eff}=5.545(t_R)^2/(W_{1/2})^2$$

It is highly desirable to provide a large number of theoretical plates, viz: $N_{eff}>1000$, because doing so normally results in a commensurately high separation efficiency.

In conjunction with combining LC with SERS, several researchers have developed methods to perform SERS measurements in flowing sample cells (G. T Taylor, S. K. Sharma, and K. Mohanan, Appl. Spectrosc., 44, 635 (1990); F. Ni, R. Sheng, and T. M. Cotton, Anal. Chem., 62, 1958 (1990); N. J. Pothier and R. K. Force, Appl. Spectrosc., 46, 147 (1992)). The first two research groups identified employed tubing to combine the flow of the analyte with SER-active silver colloids, prior to passing a SER measurement sample cell. This flow injection analysis method provided the bases for developing SERS as a detector for LC. In all cases except one (see below), standard LC columns were employed to first separate the analytes; flow injection analysis was then used to combine the column elute with silver colloids, the mixture of which was measured in a variety of flow-through sample cells (see R. D. Freeman, R. M. Hanmaker, C. E. Meloan, and W. G. Fateley, Appl. Spectrosc., 42, 456 (1988); R. Sheng, F. Ni and T. M. Cotton, Anal. Chem., 63, 437 (1991); L. M. Cabalin, A. Ruperez and J. J. Laserna, Talanta, 40, 1741 (1993); L. M. Cabalin, A. Ruperez and J. J. Laserna, Anal. Chim. Acta, 318, 203 (1996); and B. J. Kennedy, R. Milofsky and K. T. Carron, Anal. Chem., 69, 4708 (1997)); while in one case the eluted analytes were deposited as a series of drops onto a SER-active TLC plate, then measured (S. A. Soper, K. L. Ratzlaff, and T. Kuwana, Anal. Chem., 62, 1438 (1990)). In two cases, the authors report the separation efficiency in terms of theoretical plates. Sheng et al. demonstrate that four purine bases can be separated in 10 to 15 minutes, while Cabalin et al. (1993) demonstrate that three drugs can be separated in 8 to 10 minutes. The latter-named authors also quantified the separation efficiency in terms of theoretical plates, with $N_{eff}$ ranging from 860 to 2000 being deemed sufficient for analysis.

Previous research has employed primarily the three most common methods of generating surface-enhanced Raman scattered radiation; i.e., using roughened silver or gold electrodes, using silver- or gold-coated substrates, and using silver or gold colloids for detecting separated analytes. The lattermost method has gained the greatest amount of attention, since colloids can be prepared easily and inexpensively, and mixing of the colloids with the chromatographic column effluent, using flow injection, is straightforward. Care must be taken however to control aggregation of the colloids so that the amount of Raman signal enhancement is maintained. Also, a range of experimental variables, such as analyte concentration and pH, can strongly influence aggregation and, to some extent, limit applications; the choice of carrier solvent is similarly limited by the need to maintain colloid integrity.

As described by Farquharson et al. in commonly owned U.S. Pat. No. 6,623,977 (filed under application Ser. No. 09/704,818, and published as International Publication No.

WO 01/33189 A2), the entire specification of which is hereby incorporated hereinto by reference thereto, sol-gels have been developed to trap silver or gold particles as an improved method of generating plasmons for SERS (see also S. Farquharson, P. Maksymiuk, K. Ong and S. D. Christesen, SPIE, 4577, 166 (2002); F. Akbarian, B. S. Dunn and J. I. Zink, J. Chem. Phys., 99, 3892 (1995); T. Murphy, H. Schmidt and H. D. Kronfeldt. SPIE, 3105, 40 (1997); and Y. Lee, S. Dai and J. Young, J. Raman Spectrosc. 28, 635 (1997)). It is appreciated that, once the sol-gel has formed, the particle size and aggregation of the metal dopant are stabilized, albeit changes in pH may still result in variable Raman signal intensities, such as in the case of weak acids and bases, wherein the relative concentrations of the ionized and unionized forms may be influenced. Also, it has been shown that many of the common solvents, such as acetone, methanol, and water, can be used equally with these SER-active metal-doped sol-gels in generating SER spectra of analytes.

In accordance with other recent developments, moreover, sol-gels have been used as the stationary phase in columns for liquid- and gas-phase chromatography, affording advantages in both the preparation of columns and also in their performance. The sol-gel approach enables deactivation, coating, and immobilization to be combined as a single step, while the sol-gels have found broader application to solvents and analytes.

Microchip devices have also been employed for effecting chemical separations (see S. C. Jacobson, R. Hergenröder, L. B. Koutny, and J. M. Ramsey, Anal. Chem., 66, 1114 (1994); S. C. Jacobson, R. Hergenröder, L. B. Koutny, R. J. Warmack, and J. M. Ramsey, Anal. Chem., 66, 1107-1113 (1994); S. C. Jacobson, R. Hergenröder, L. B. Koutny, and J. M. Ramsey, Anal. Chem., 66, 2369 (1994); and A. W. Moore, Jr., S. C. Jacobson, and J. M. Ramsey, Anal. Chem., 67, 4184 (1995)).

It is clear from the foregoing background disclosure that chromatography and SERS can be combined to achieve trace chemical analysis of multiple analytes in a sample. It is also clear that separation materials used in TLC can be coated with silver to combine chemical separation and SER-activity, albeit the separation process is slow (sp. 40 to 45 minutes), and the SER-activity is modest. Furthermore, the foregoing disclosure indicates that modest improvements in analysis time (sp. 10 minutes) and SER-activity can be made by adding silver colloids to the effluent of liquid chromatography columns.

No one skilled in the art of TLC or LC suggests using transparent containment means to hold a material that has the combined abilities of performing chemical separation and exhibiting SER-activity, so that Raman spectroscopy can be used to make measurements at discrete points or continuously along the length of the containment means, as this would not provide any advantage over the TLC or LC methods described. Knowledge of the prior art would indicate that, in the latter case (i.e., LC), the Raman measurement would still be best performed at the end of the column, where efficient separation has been achieved, as defined by a high number of theoretical plates. Indeed, Nirode et al. (W. F. Nirode, G. L. Devault, and M. J. Sepaniak, Anal. Chem., 72, 1866 (2000)) describe measuring SER spectra of separated analytes as they flow by the end of an electrophoresis column. In that method, silver colloids were added to a running buffer containing the mixed analytes, which flowed through a capillary connecting the anode and cathode of an electrochemical cell. Although measurements along the length of the column might conceivably have been performed (if the structurally supporting coating were etched away at several positions, thereby most likely rendering the column too fragile to be of use), analyte separation prior to the column exit point is incomplete; and more importantly, the analytes are moving, making it implausible to know where along the column, or when, to make such measurements. The same would be true for LC, and thus no advantage would be expected.

In no case does the foregoing background information teach or remotely suggest rapidly drawing a sample into a transparent column, capillary, or channel that contains a combined chemical separation and SER-active medium, to afford effective distribution and rapid separation of chemical analytes along the length of such containment means, so that the analytes can be quickly detected and measured by Raman spectroscopy at a plurality of points along the length of the containment means. One skilled in the art of chromatography would not expect to achieve the extraordinary level of detection and discrimination capability that is afforded by the present method and apparatus, based for example upon a characterization of the invention in terms of the number of theoretical plates presented for analyte chemical separation to allow identification of the analytes.

SUMMARY OF THE INVENTION

It is the broad object of the present invention to provide a novel method and apparatus for the qualitative and quantitative analysis of chemicals in solution.

A more specific object of the invention is to provide such a method and apparatus by which at least one analyte chemical can be rapidly separated from a sample solution, and quickly detected.

It has now been found that certain of the foregoing and related objects of the invention are attained by the provision of a method comprising the steps:

providing a sample solution containing a plurality of chemicals, including at least one analyte chemical;

providing containment means that is sufficiently transparent to excitation radiation, at least at a plurality of locations, to permit transmission of excitation radiation effective for generating measurable amounts of surface-enhanced Raman scattered radiation, and that is sufficiently transparent to such scattered Raman radiation, at least at said plurality of locations, to permit transmission of measurable amounts of such scattered Raman radiation, the containment means containing a stationary medium comprising or defining an elongate path, for the sample solution, that is functional to separate at least the one analyte chemical and also exhibiting surface-enhanced Raman scattering activity, the plurality of locations being along the elongate path;

introducing into the containment means a quantity of the sample solution, undiluted by any carrier fluid, at a location adjacent one end of the elongate path;

applying a driving force to promote flow of the sample solution away from the location of introduction and to effect distribution of the sample solution through the stationary medium, along the elongate path and in sufficiently intimate contact with the stationary medium to thereby effect separation of the at least one analyte chemical from the sample solution, such that distribution of the sample solution and consequential separation of the at least one analyte chemical are effected in a period that does not exceed five minutes, which period commences at the time the quantity of sample solution has been introduced into the containment means;

quickly thereafter irradiating, with excitation radiation, the medium and the sample solution distributed thereon, at least at the plurality of locations along the path, to generate surface-enhanced Raman scattered radiation, and detecting at least a portion of the surface-enhanced Raman scattered radiation at each of the plurality of locations; and ultimately analyzing the detected radiation to determine the presence of the at least one analyte chemical in the sample solution.

In preferred embodiments of the method, the period for effecting distribution of the sample solution, and consequential separation of the at least one analyte chemical, will not exceed thirty seconds, and most desirably that period will not exceed about one second. Separation efficiency can be increased by heating the stationary medium to a temperature significantly above ambient (e.g., to 25° to 50° C.). The step of irradiating the medium and sample solution, and detecting the surface-enhanced Raman scattered radiation, will preferably be completed during a second period that does not exceed one hour, also commencing at the time the quantity of sample solution has been introduced into the containment means; more preferably the second period will not exceed five minutes, and most desirably it will not exceed about one minute.

At the completion of the step of applying a driving force, at least a major proportion of the sample solution will normally have been distributed on the stationary medium, and will remain thereon. The method avoids the use of any carrier fluid (liquid or gas) for the analyte sample, thereby simplifying the process (and apparatus used for performing it), maximizing the concentration of analyte chemicals in the liquid phase, and maximizing the strength of the Raman scattered radiation signals detected. The step of analyzing the collected radiation will desirably occur within 24 hours following the time when the sample solution has been introduced into the containment means.

The method of the invention may more specifically be characterized to afford an effective separation efficiency that substantially exceeds that which would be indicated by the number of theoretical plates, $N_{eff}$, determined to be necessary for establishment of the required multiple, successive phase equilibria, in accordance with the expression:

$$N_{eff} = 5.545(d_R)^2/(W_{1/2})^2,$$

wherein $d_R$ is the retention distance, from the location of introduction into the stationary phase medium, at which separation of the at least one chemical from the sample solution occurs, and $W_{1/2}$ is the width, at half height, for the peak of a distributed analyte chemical in a plot of the intensity of surface-enhanced Raman-scattered radiation, as a function of distance, detected in the detecting step. In preferred embodiments of the invention the value of N will not exceed 100, and preferably it will not exceed 25.

In accordance with certain embodiments, the stationary medium may comprise at least one separation material admixed with at least one surface-enhanced Raman active material. The SER-active material may desirably be of particulate form, advantageously comprised of metal-doped sol-gels, metal-coated particles of polystyrene, silica, alumina or titania, particularly spheres of submicron size, or metal nanoparticles; the SER-active material may also comprise a fixed surface deposit.

The SER-active metal, utilized for affording surface-enhanced Raman scattering activity will normally be silver, gold, copper, or an alloy or mixture thereof. The metal will usually be of particulate form, preferably of submicron size, with the particles being either substantially isolated from one another or grouped for possible improvement of SER scattering. Such groupings can range from random to ordered, such as aggregates or patterned arrangements (e.g., linear or branched). The particles may comprise metals, metal colloids, hollow metal spheres (shells), or metal-coated spheres of, for example, polystyrene, silica, alumina, zirconia or titania. The surface-enhanced Raman active metal may alternatively comprise individual elements of substantially regular (e.g., Y-shaped, linear, etc.) character.

The separation material employed will be in the form of particles, matrices, gels, sol-gels, or integral elements, the latter taking the form of one or (more commonly) a plurality of porous plugs or membranes, or a fixed surface deposit. The separation material will generally be selected from the materials used in chromatography, i.e., gas, liquid, HPLC or thin layer chromatography. This group includes, but is not limited to, aero-gels, zero-gels, metal alkoxide-based sol-gels, silica gels, transition metal-stabilized silica, derivatized silica-based matrices, glass beads, long-chain alkanes, derivatized long-chain alkanes, polymers, derivatized polymers, functionalized membranes, alumina, size-exclusion resins, ion-retardation, and ion-exchange resins. In certain instances the stationary medium will advantageously comprise at least one separation material combined with at least one surface-enhanced Raman active material. When both the SER active material and also the separation material are of particulate form, they will normally constitute a homogeneous mixture in which the separation material is present in a volumetric ratio to the surface-enhanced Raman-active material in the range of about $1 \times 10^6:1$ to $1:10^2$.

Other objects of the invention are attained by the provision of apparatus for carrying out the analysis of a sample solution containing a plurality of chemicals, including at least one analyte chemical, effected with the rapid separation and quick detection of the at least the one analyte chemical, and in cooperation with flow-promoting, driving force-producing means, wherein the apparatus comprises the combination:

containment means for containing a stationary medium and being sufficiently transparent to excitation radiation, at least at a plurality of locations, to permit transmission of excitation radiation effective for generating measurable amounts of surface-enhanced Raman scattered radiation, and being sufficiently transparent to such scattered Raman radiation, at least at the plurality of locations, to permit transmission of measurable amounts of such scattered Raman radiation;

a stationary medium, functional to separate from the sample solution, in intimate contact therewith, the at least one chemical contained in the sample solution and also exhibiting surface-enhanced Raman scattering activity, the stationary medium being contained in the containment means and comprising or defining an elongate path for the sample solution through the containment means and past the plurality of locations, the stationary medium being of such character as to promote intimate contact with a sample solution flowing along the flow path;

means defining an entrance into the containment means for introducing a sample solution at a location adjacent one end of the flow path, the plurality of locations being spaced from the entrance along the containment means; and means defining an exit adjacent the opposite end of the flow path, with at least one of the means defining an entrance into the containment means and the means defining an exit adjacent the opposite end of the flow path being adapted for connection of driving force-producing means for promoting flow of the sample solution, away for the location of introduction, and for effecting distribution of the sample through the stationary medium, along the elongate path, and consequential rapid separation of the one analyte chemical.

One or more suitable optical devices, capable of delivering excitation radiation and collection of Raman photons, scan the length of a suitably transparent column, or monitor it along its effective length (i.e., the length of the stationary separation/SER-active medium) or at a plurality of discrete locations, for detection of the distributed chemical species, thereby enabling detection to be completed quickly and a complete analysis to be accomplished in five minutes or less; such an optical device may comprise a lens (which may for example be aspherical, spherical, cylindrical, etc., as will be evident to those skilled in the art), a microscope objective, a fiber optic probe, etc. The rate at which the chemical and physical contact necessary for effecting distribution of the species occurs is promoted by driving the analyte solution through or along a bed, a filled section or a deposit of the stationary, chemical-separation and SER-active material, under applied positive or negative pressure. As indicated above, distribution of the sample solution, and consequential separation of the analyte chemical (or chemicals), occurs in a period that does not exceed one minute, that preferably does not exceed ten seconds, and that most desirably does not exceed about one second. Irradiation, and detection of SER-scattered radiation is desirably accomplished in an hour or less (after which the analyte separation may deteriorate and thereby compromise the ultimate analysis); preferably, irradiation and detection will occur in five minutes or less and most desirably in one minute or less. Actual analysis of measured spectra (collected radiation) can be deferred for an extended period of time, but normally the results will be wanted within about one hour's time, or sooner.

The apparatus may comprise a packed or otherwise filled capillary or column of the stationary medium or, as an alternative, it may comprise a channel on a microchip card substrate. In such alternative embodiments the elongate containment means may take the form of a microchannel in the substrate or a capillary tube on the substrate, and the substrate may itself have one or more ports, or other structural features, communicating with the channel and providing entrance-defining means, exit-defining means, and means for accommodating overflow, or excess sample volume. It should be appreciated that the sample will not normally be drawn entirely through the SER-active medium, and indeed will preferably remain distributed thereupon; in many instances therefore, any exit provided may simply serve to enable access for generating the necessary driving (e.g., vacuum) force. The stationary medium will advantageously comprise a lining deposited on a wall of the channel or tube, and/or a filled section contained within the channel or tube, defining the sample flow path. Additional features and functions may advantageously be incorporated into and implemented by the apparatus of the invention, as will be apparent to those skilled in the art from the description herein provided.

The instant invention uniquely combines two functions; i.e., (1) the ability to distribute samples efficiently and thereby rapidly separate chemicals therefrom, and (2) the ability to promote SER scattered radiation from chemicals in solution, which combination in turn enables analyses to be performed in a quick, highly effective and highly efficient manner. Although the sol-gels (and other media) described advantageously combine both functions in a single material, it will be appreciated from the present description that two or more different materials can be mixed or combined to the same end.

DETAILED DESCRIPTION OF THE PREFERRED AND ILLUSTRATED EMBODIMENTS

Except where otherwise indicated, the silver-doped SER-active sol-gels employed in the examples that follow were prepared in accordance with the method of Farquharson et al. U.S. Pat. No. 6,623,977. In essence, a silver amine complex, consisting of a 5:1 v/v solution of 1 N $AgNO_3$ and 28% $NH_3OH$, is mixed with an alkoxide, consisting of a 2:1 v/v solution of methanol and tetramethyl orthosilicate (TMOS) in a 1:8 v/v silver amine to alkoxide ratio.

As an example of one fabrication technique that can be used in the practice of the invention, a 0.15 mL aliquot of the foregoing mixture was transferred to a 2 mL glass vial, which was spun to coat its inside walls. After sol-gel formation, the incorporated silver ions were reduced with dilute sodium borohydride, followed by a water wash to remove residual reducing agent. The sol-gel coating was scraped from the walls of the vial, and was converted to a homogeneous powder by grinding with a mortar and pestle.

Figure 1:
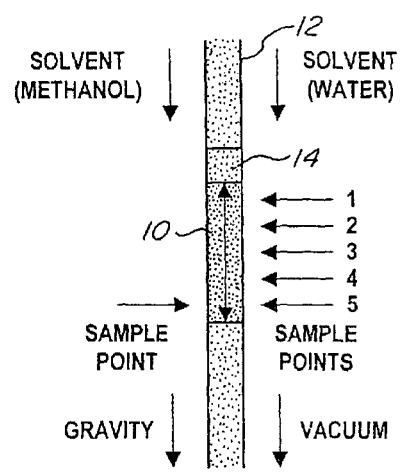
FIG. 1 is a diagrammatic representation of a packed bed column used for separation and analysis of dissolved analytes, showing both the traditional, gravity-flow (with inherent capillary action) method of solution transport, with a single sampling point, and also a vacuum-assisted transport method with, in accordance with a unique feature of the present invention, multiple sampling points.

As depicted in FIG. 1, the ground sol-gel 10 was packed into a 5 mm length of a 4 cm length of a 1.0 mm diameter melting point capillary tube 12, using a sterile cotton plug 14 to hold the powder in place, and the top was fit with a 1.0 mL disposable plastic pipette (not shown) to allow delivery of 10 μL samples to the rudimentary liquid chromatography column so prepared. A diaphragm pump (also not shown) was disposed at the exit end of the column, to enable operative attachment for vacuum-assisted introduction of the test solution into the sol-gel bed, and distribution thereupon, as herein described.

The column was fixed vertically at the focal point of a microscope objective (20×) attached to an XYZ positioning stage, to focus the beam into the sample and to collect radiation scattered back along the axis of incidence. A notch filter was provided to reflect the excitation laser beam to the microscope objective, and to pass the collected Raman-scattered radiation.

Two 3 m lengths of fiber optic were used to deliver the laser energy (200 micron diameter) and to collect the Raman-scattered radiation (365 micron diameter). A Nd:YAG laser provided 50 mW of 1064 nm excitation radiation at the sample, and a Fourier transform Raman spectrometer, equipped with an InGaAs detector, was used for spectra acquisition. Of course, other suitable Raman analyzers, with lasers exciting at different wavelengths, can be used in appropriate circumstances.

EXAMPLE ONE

Insofar as the flow of analyte solution is concerned, the following experiment (depicted along the left side of FIG. 1) mimics traditional liquid chromatography. A solution of $8 \times 10^{-3}$M p-aminobenzoic acid and $4 \times 10^{-3}$M phenyl acetylene was prepared in methanol to demonstrate separation of polar and non-polar chemicals. A 10 µl quantity of the solution was added to the top of a separation and analysis column, constituted and assembled as hereinabove described. A 1 mL quantity of methanol was added as a carrier solvent, and allowed to elute under the forces of gravity and capillary action only. Using an optical probe coupled to a Raman spectrometer, which measured the surface-enhanced Raman spectra at the bottom of the column as a function of time, it was confirmed that the methanol solvent caries the non-polar PA through the column ahead of the polar PABA.

Figure 2:
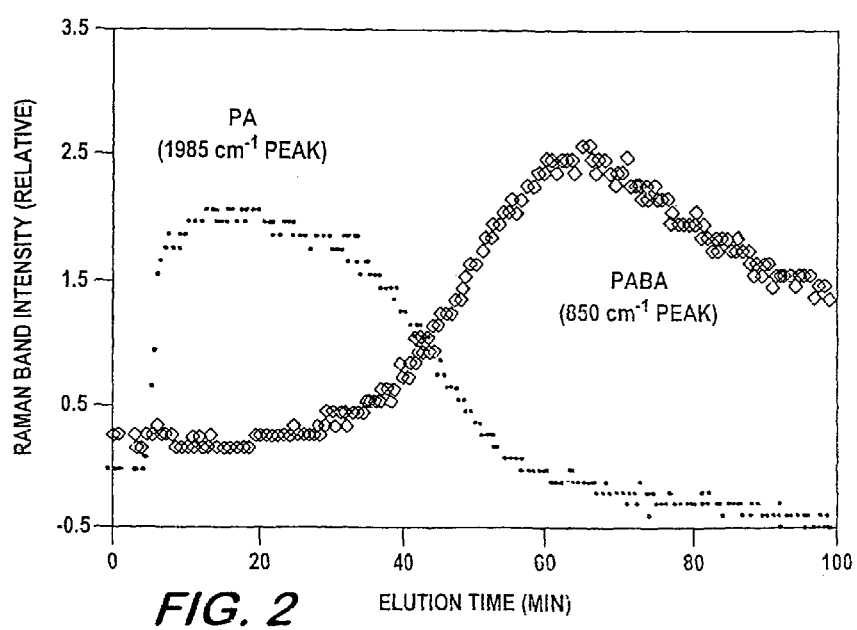
FIG. 2 is a plot of Raman band relative intensity over a period of 100 minutes, constituting an elution profile of phenyl acetylene (PA) and p-aminobenzoic acid (PABA)

More specifically, the microscope objective was positioned 0.5 mm from the bottom edge of the 5 mm length of packed sol-gel, and scans were made and averaged every 30 seconds to produce spectra. Unique Raman peaks for PA and PABA, at 1985 $cm^{-1}$ and 850 $cm^{-1}$, respectively, were used to plot relative concentration as a function of time. FIG. 2 shows the elution profiles generated for both analytes during a 100-minute test period, which verify that chemical separation does occur. These data also show however that, in the absence of any external driving force, a significant period of time is required. Furthermore, examination of the retention times, 18 and 64 minutes, and peak widths at half height, 36 and 43 minutes, indicate $N_{eff}$ values of 2.8 and 12.3 for PA and PABA, respectively, demonstrating that the separation efficiency of the column was very poor. According to theory, the separation efficiency can be improved by slowing the flow rate to allow greater times for equilibria, between the mobile and stationary phases, to be established for the analyte.

EXAMPLE TWO

This example demonstrates that techniques can be applied for driving the solution through the column to substantially reduce the distribution and separation time, and thereby the overall analysis time. Thus, a second experiment (depicted along the right side of FIG. 1) employed an identical sample but used a 50/50 v/v mixture of methanol and water as the carrier solvent, rather than methanol alone. In addition, a vacuum of 50 cm of Hg was applied for 30 seconds to draw the sample into the column. Due to the addition of water in the solvent, the separation was reversed because, in the present case, the alkoxide, TMOS, used to prepare the sol-gel is hydrophilic (i.e., water carries the polar PABA along the SER-active medium first), demonstrating flexibility of the concept.

Since the entire length of the packed sol-gel bed was SER-active, moreover, the extent of distribution and separation could be, and was (in accordance with a feature of the instant method), measured by moving the microscope objective to five different positions along its length, enabling the collection of spectra at each position. More specifically, spectra, plotted in FIG. 3, were collected at five discrete points, spaced 1 mm apart, the first being located at a level 0.5 mm from the top edge of the sol-gel bed, with each spectrum consisting of scans averaged for 30 seconds. Spectra (1) and (5), obtained at the top and bottom of the column, indicate pure PA and PABA, respectively; the intermediate spectra represent mixtures of the two analytes.

Because there was no need to wait for the analytes to elute past a single measurement point at the end of the column (i.e., the partially or fully separated chemicals could be measured wherever they occurred along the column), each analyte was identified quickly; complete analysis was performed in three minutes, as compared to at least 80 minutes using the traditional method. The time savings realized provides many significant benefits, particularly for trace chemical analyses of multi-component systems.

These results are completely unexpected, since quickly drawing the sample into the sol-gel, at nearly 200 times the rate at which it would flow under the force of gravity alone, would further reduce the time for the analytes to come to equilibrium between the two phases (i.e., the solvent and the separation medium). This means that, from a theoretical standpoint, the number of hypothetical layers for establishing equilibria would be dramatically reduced, and effective separation and identification of the analytes along the column should therefore be entirely unlikely.

Figure 3:
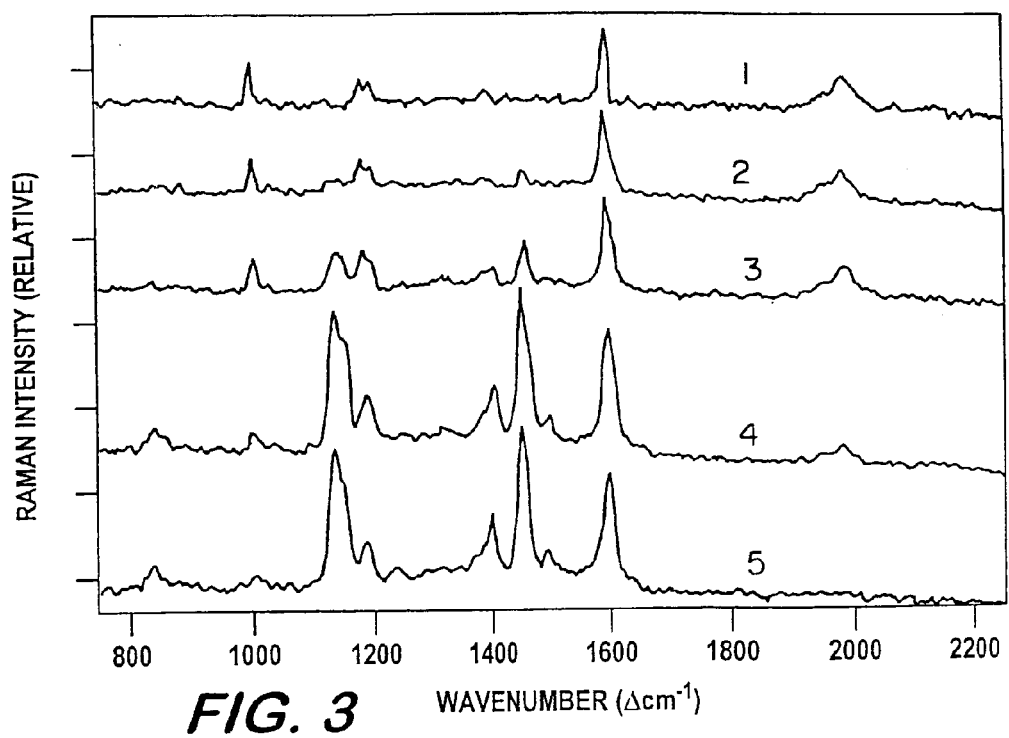
FIG. 3 presents a series of spectra, taken at five points along the length of a sol-gel packed column, representing a preferred embodiment of the invention, used for separation and measurement of concentrations of PA and PABA.

The series of spectra presented in FIG. 3 also demonstrate the power of Raman spectroscopy, in that each chemical can be easily identified, either isolated or as a mixture. Although previous knowledge of, or expectation as to, the sample composition simplifies the task, spectral matching and deconvolution software programs, or like techniques, can be used to handle unknown components.

EXAMPLE THREE

Figure 5:
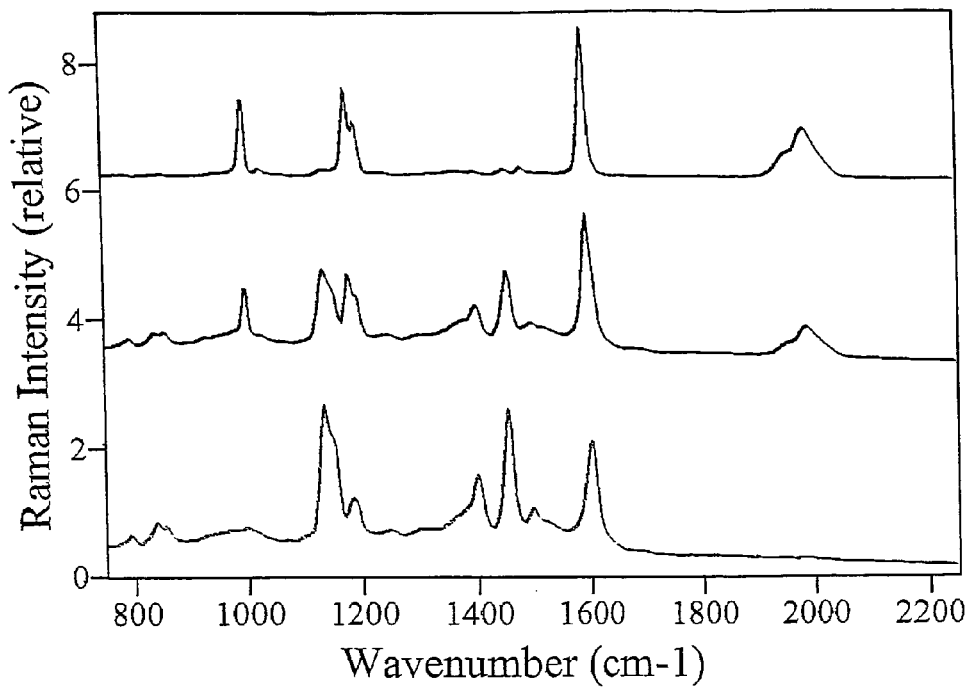
FIGS. 5, 7, 9, and 10 are SER spectra demonstrating separations effected in accordance with examples hereinafter set forth.

As a variant of the system used in Examples One and Two (which employed a silver-doped TMOS-based sol-gel, scraped from the wall of the vial in which it is prepared and packed into a 1 mm diameter glass capillary), this example employs sol-gels that have been gelled and reduced in the capillary. FIG. 5 shows spectra in which the distribution and separation of a mixture of PABA and PA, each at one part per million, was effected. The mixture was prepared by dilution from equal volumes of a solution of 1 mg PABA in 1 mL water, and 0.1 mL PA liquid mixed in 0.9 mL methanol; the sol-gel was prepared from octadecyl silane (ODS) a non-polar stationary phase.

Figure 9:
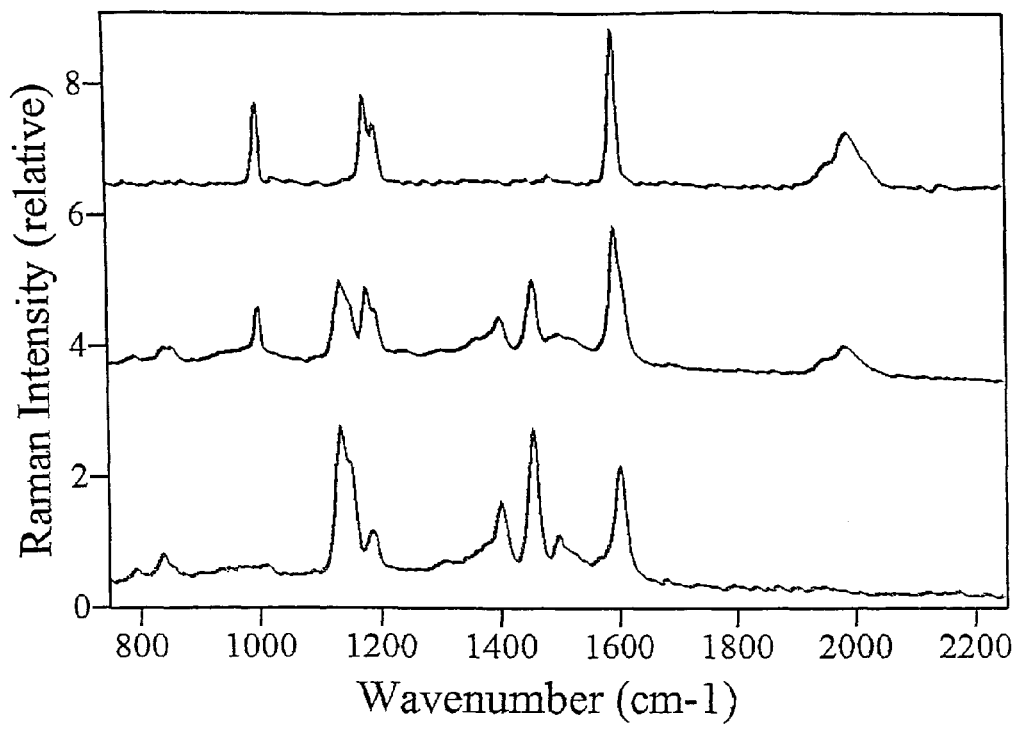

A 10 microL sample, undiluted by any carrier fluid, was drawn into a 3 cm length of SER-active sol-gel, contained in a 1 mm glass capillary, in 30 seconds using a syringe pump to precisely control the flow rate and effect rapid distribution and separation. The capillary was mounted in front of an objective lens, and spectra were recorded at 30 discrete positions, each spaced 1 mm apart along its length. In this case a 785 nm diode laser was used for excitation, further demonstrating flexibility of the present invention. Quality spectra were obtained at each point by averaging accumulated spectra for 10 seconds, albeit 1 second would suffice in the present example, as demonstrated for example in FIG. 9 (the procedure for the generation of which was otherwise substantially the same as for FIG. 5).

The top, middle, and bottom spectra in FIG. 5 were collected, respectively, at locations spaced 7, 14, and 21 mm from the sample entry point (i.e., the entrance end of the sol-gel bed). The polar PABA (bottom spectrum) readily flows past the non-polar ODS sol-gel, while the non-polar PA (top spectrum) lags behind as it interacts strongly with the non-polar ODS.

As mentioned in connection with Example Two, the time used to introduce and distribute the sample along the capillary, and separate the analyte chemicals, is insufficient for the analyte chemicals to come to equilibrium between the solvent and stationary phases, and effect efficient separation, in regard to theoretical plates. This is demonstrated by measuring spectra at 1 mm intervals along the length of the capillary, 28 in all, and calculating the number of theoretical plates (using however an equation that was suitably modified from the conventional expression, provided above). As in the previous example, the unique Raman peaks for PA and PABA, at 1985 $cm^{-1}$ and 850 $cm^{-1}$, respectively, were used to plot relative concentration, this time as a function of position along the length of the capillary. It should additionally be realized that other Raman peaks, such as those at 1000 and 1130 $cm^{-1}$, can also be used to measure PA and PABA, respectively, to the same end.

Figure 6:
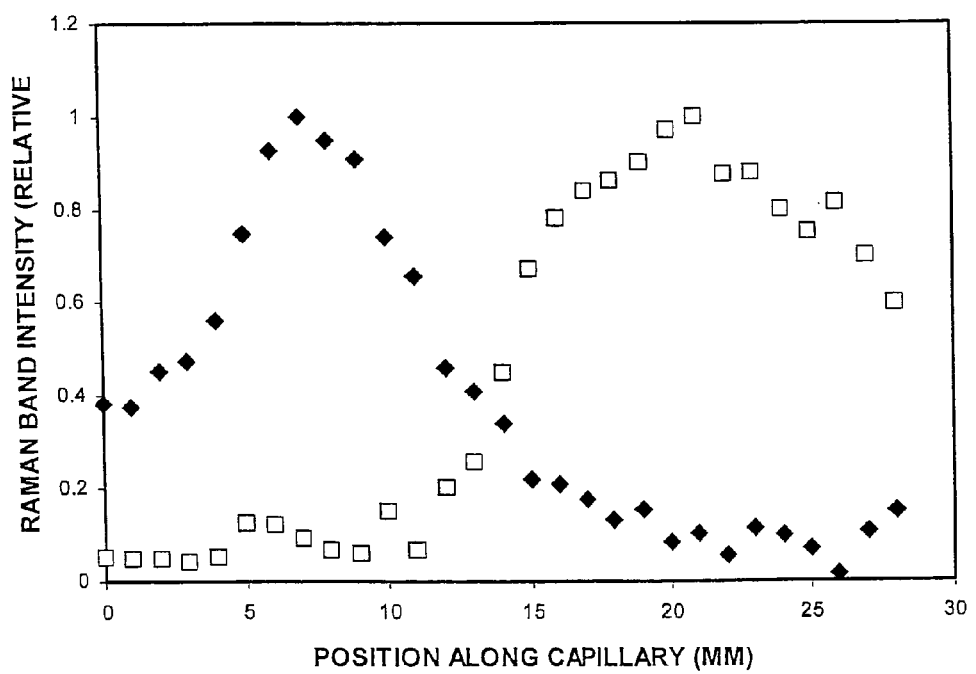
FIGS. 6 and 8 are plots showing distribution profiles of analytes over the lengths of capillaries containing solid separation and SER-active media.

FIG. 6 shows a distribution profile generated for both analytes over the 3 cm capillary length described, which verifies that chemical separation does occur. In this case, the number of theoretical plates, $N_{eff}$, can be calculated using the retention distance, $d_R$, along the capillary instead of the retention time, and the width at half height, $W_{1/2}$, for the peak of a distributed analyte, according to the expression (more fully defined above):

$$N_{eff} = 5.545(d_R)^2/(W_{1/2})^2$$

Accordingly, the retention distances, 7 and 21 mm, and peak widths at half height, 7 and 13 mm, indicate $N_{eff}$=5.5 and 14.5 for PA and PABA, respectively. Unexpectedly, these values are similar to those obtained using elution, yet the time to distribute the sample along the capillary, 30 seconds, is approximately 200 times faster than the time required to elute the samples through a similar capillary, 100 minutes, following standard LC procedures. Nevertheless, the distribution is shown to be sufficient to allow Raman spectra unique to each analyte to be obtained at some positions.

Figure 7:
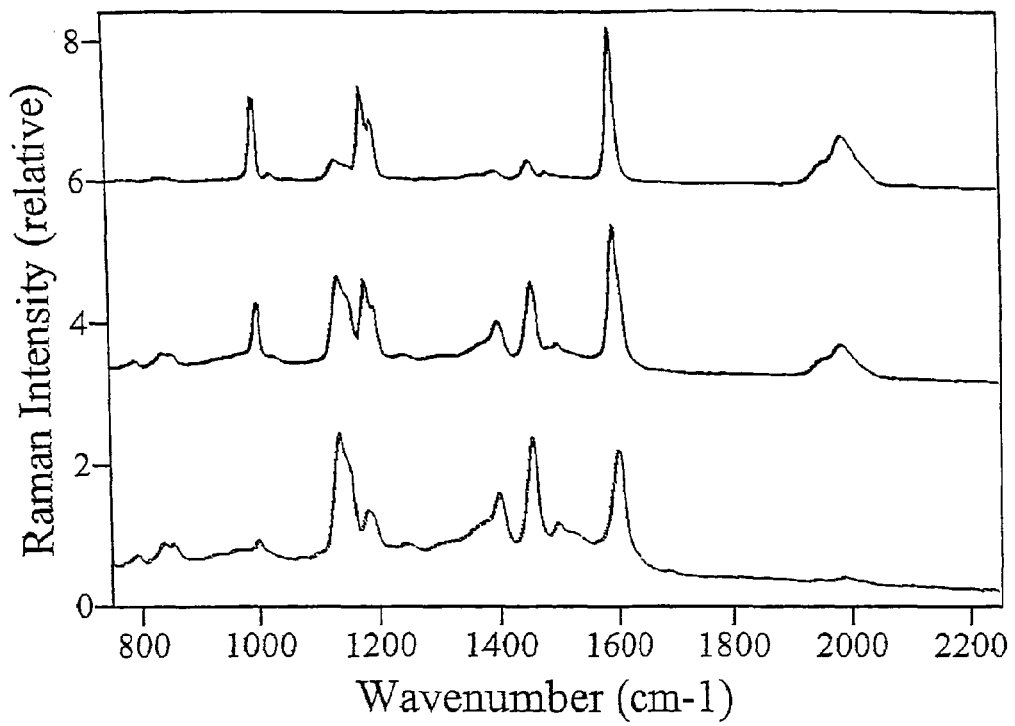
Figure 8:
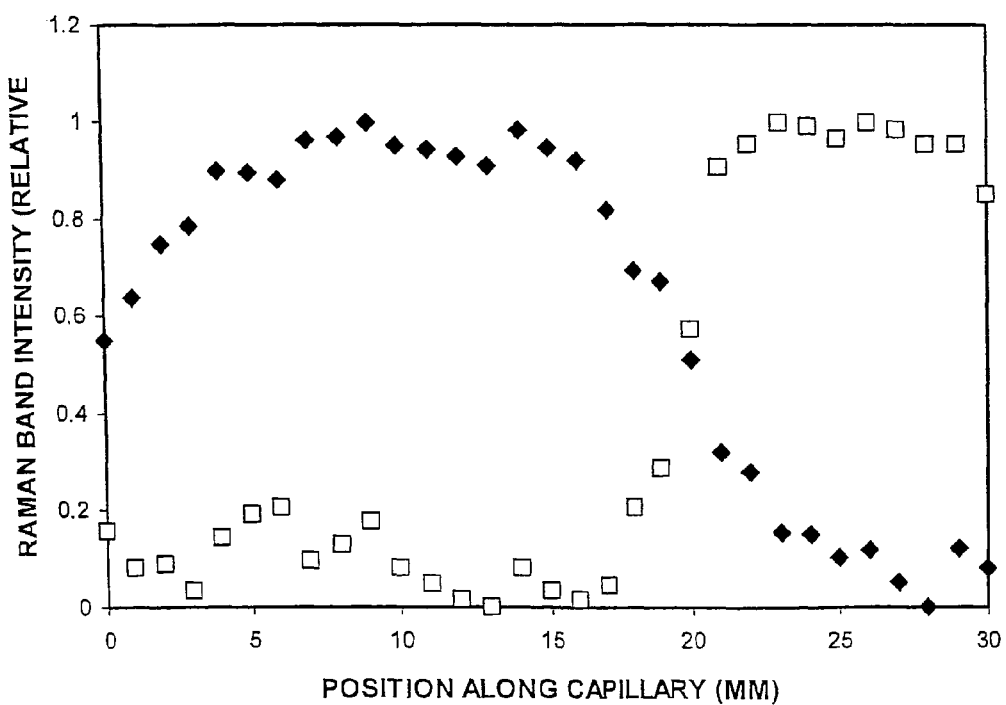

To further demonstrate these unexpected results, a syringe was used to draw a sample, identical to the sample hereinabove described, into a second identical capillary, in one second, whereby near instantaneous distribution and analyte chemical distribution and separation were achieved. Again, PA and PABA distribute along the 3 cm of SERS-active sol-gel, producing unique spectra at 12 and 26 mm, with a mixture occurring at 20 mm, as shown by the top, bottom, and middle spectra, respectively, in FIG. 7. A plot of the respective Raman peak heights, depicted in FIG. 8, allows the number of theoretical plates to be determined and to have values of 2.0 and 14.6, respectively. Although it is clear that the separation is less complete, the two analytes can easily be identified, and the separation time has decreased an additional 30 fold, to be essentially 6000 times faster than traditional chromatography.

EXAMPLE FOUR

This example demonstrates alternative methods for adding SER-active metals to separation materials, in accordance with the present invention.

Part A

Figure 10:
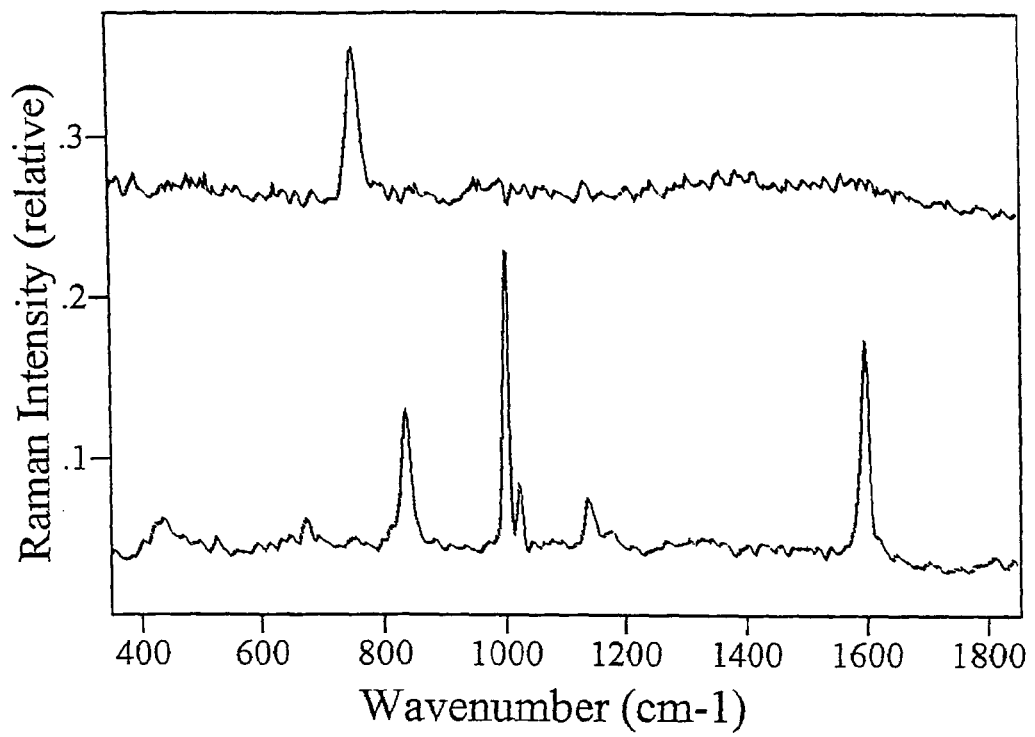

An MTMS-based sol-gel was used to fill a 2 cm length of glass capillary and, following gelation, an approximately $10^{-3}$M silver colloid solution, prepared according to literature methods (e.g., P. C. Lee and D. Meisel, J. Phys. Chem., 86, 3391, 1982), was drawn by syringe through the sol-gel. After waiting for about five minutes, a 0.5 µL one-to-one volume mixture containing benzoic acid (BA) and methyl phosphonic acid (MPA), each at 0.5 mg/mL in water, was drawn by syringe, in one second, into the SER-active capillary thus produced. FIG. 10 shows the SER spectra of each analyte (MPA at the top, BA at the bottom) measured at 0.25 cm and 1.5 cm respectively from the front end of this sol-gel segment containing silver colloid.

Part B

The procedure of Part A is substantially repeated, using however silica gel in place of the sol-gel described and allowing a longer period for stabilization (although reduced stability may be accommodated because the sample is not drawn entirely through, and out of, the capillary). Comparable separation and analytical results are achieved.

Part C

As a further variation, a glass capillary is internally coated with a silver-doped sol-gel, and a quantity of silica gel is thereafter introduced to fill the bore defined within the sol-gel lining, and thereby afford added separation capability. The resulting structure is found to function effectively for rapid separation of analyte chemicals, and for quick detection and analysis by SERS.

EXAMPLE FIVE

Figure 4:
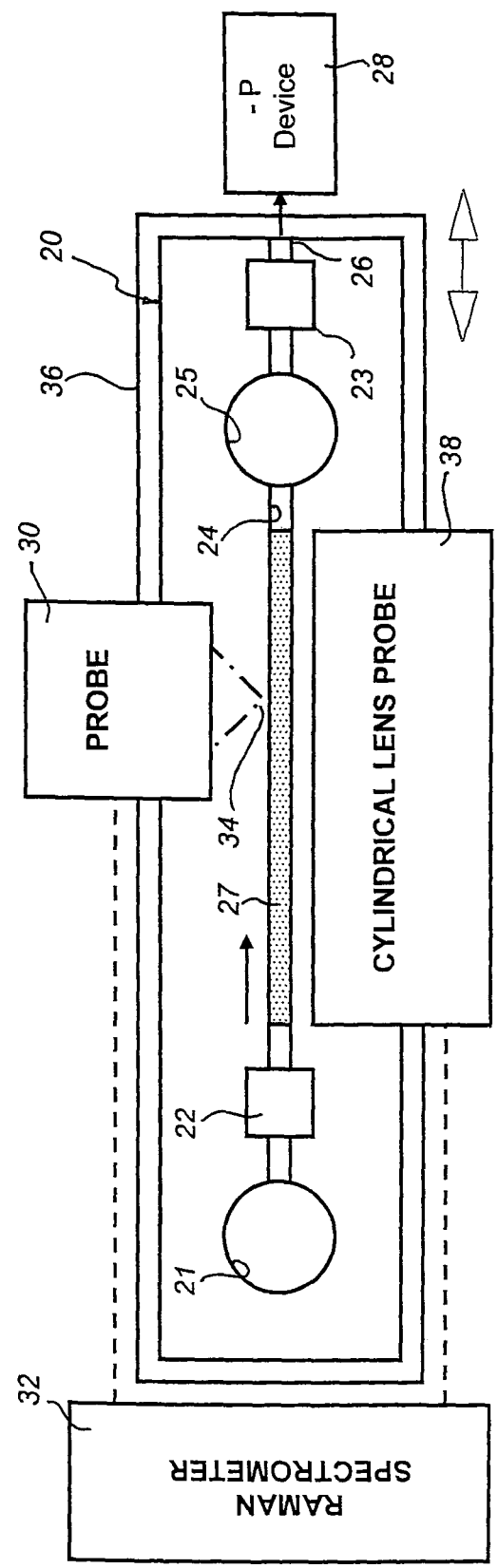
FIG. 4 is a diagrammatic representation of a microchip device, incorporating a microchannel containing a SER-active sol-gel chemical separation medium, which embodies, and is enabled by, the present invention and is used in association with a Raman spectrometer apparatus.

A microchip chemical analyzer, diagrammatically illustrated in FIG. 4, constitutes a form of apparatus embodying, and enabled by, the present invention. The analyzer comprises a card-sized platform (e.g., one to five inches long), generally designated by the numeral 20, which contains a sample input port 21, valves 22 and 23, an excess sample chamber 25, and a microchannel 24, a central section 27 of which channel is comprised of a metal-containing SER-active sol-gel which takes the form of a porous lining deposited on the wall of the channel 24 (albeit a packed channel or other SERS active and separation materials are also feasible). The analyzer is constructed so that a negative pressure driving force (e.g., vacuum), applied by a device 28, connected by suitable means (not shown) at the exit end portion 26 of the microchanel 24, and acting through the chamber 25 (which is otherwise closed), will promote rapid passage of a sample into the channel 24 as well as promoting the physical and chemical contact required for effective distribution through the medium in the section 27, and separation.

In use, a sample (e.g., a drop of blood) is applied to a porous cover (not shown), such as a membrane or sponge overlying the sample entry port 21 (or the port may be of septum-like form), typically using an eye dropper, a pipette, or a syringe. The sample is then urged (by negative pressure, as described, or alternatively by positive pressure, such as may be applied by pipette, syringe, or the like at the opposite end) into the SER-active central section 27 of the microchannel 24; any excess, or overflow, of the sample will normally be accommodated in the chamber 25, and will not exit from the analyzer. Chemical components of the distributed sample interact with the sol-gel deposit (the affinity for which components may be enhanced by the metallic element of the sol-gel, as noted below), and are thereby rapidly separated. The target analytes can then be identified and quantified by SER spectroscopy, using a scanning probe 30 of an operatively connected Raman spectrometer 32, which includes appropriate interface optics for producing a focus at 34. Valves 22 and 23 are included to control the vacuum (or pressure) applied to the microchannel 24, as necessary or may be desired. The microchip card 20 would typically fit onto, and be mounted upon, a positioning stage 36 associated with the Raman spectrometer 32, which aligns interconnects for the sample delivery and the flow-control system, including valves 22 and 23 and the vacuum device 28, and that dynamically positions the analyzer relative to the Raman focus 34 to enable spectral analyses to be effected along the length of the SER-active portion 27 of the channel 24, as described.

It will also be appreciated that, in those instances in which a sol-gel is used as the SER-active separation medium in the practice of the present invention, virtually any sol-gel, in powdered, particulate or other finely divided form, or in the form of a porous, passage-defining deposit, can be employed. Selectivity may be afforded by the inherent electro-potential of the metal dopant (electronegative or electropositive) and/or by the hydrophobic or hydrophilic nature of such a sol-gel medium, etc. Thus, while certain of the examples set forth above employ a silver-doped sol-gel, doping with gold is regarded to be equally important; copper, and less desirably nickel, palladium, and platinum, and alloys and mixtures thereof, can of course be utilized as well.

The literature describes a number of methods by which SER-active materials, suitable for use in the practice of the present invention, can be produced. For example, a paper entitled "Surface-Enhanced Raman Spectrometry for Trace Organic Analysis" (T. Vo-Dinh, M. Y. K. Hiromoto, G. M. Begun, and R. L. Moody, Anal. Chem. 56, 1667, 1984) describes a method for preparing SER-active substrates using submicron size silver-coated spheres deposited on filter paper substrates; a paper entitled "Titanium Dioxide Based Substrate for Optical Monitors in Surface-Enhanced Raman Scattering Analysis" (J. M. Bello, D. L. Stokes, and T. Vo-Dinh, Anal. Chem., 61, 1779, 1989) describes an optical monitor consisting of a glass plate coated with $TiO_2$ and covered with a silver layer (which coating could be removed and employed as particulate material in the practice of the present invention); in a paper entitled "Surface-Enhanced Raman Analysis of p-Nitroanaline on Vacuum Evaporation and Chemically Deposited Silver-Coated Alumina Substrates" (Y.-S. Li, T. Vo-Dinh, D. L. Stokes, and Y. Wang, Appl. Spectrosc., 46, 1354, 1992) vacuum thermally evaporated and chemically prepared silver-coated alumina substrates are described; and in a paper entitled "On-Line Spectroscopic Characterization of Sodium Cyanide with Nanostructured Gold Surface-Enhanced Raman Spectroscopy Substrates (P. M. Tessier, S. D. Christesen, K. K. Ong, E. M. Clemente, A. M. Lenhoff, E. W. Kaler, and O. D. Velev, Appl. Spectrosc., 46, 1524, 2002), a technique is described for producing SERS substrates by the deposition of metallic nanoparticles on a substrate using gold nanoparticles and polystyrene microspheres. Needless to say, these and other suitable techniques, such as metal shells of spheric or other form, can be employed to produce substrates and particulate materials effective for use in practicing the invention, utilizing any of the several SER-active metals disclosed herein.

As indicated above, the SER-active particles (e.g., of silver or gold) can be prepared by any suitable means, mixed with a suitable stationary medium for effecting chemical separation, and introduced into a suitable enclosure, such as a glass tube, capillary, or channel. Alternatively, the SER-active material may be coated upon the container walls, with a particulate adsorbent material filling the space therewithin, or the separation material may take any other suitable form, as indicated hereinabove.

The nature and structure of the containment vessel can vary widely, and is not limited to columns; for example (and as has been described), the analysis apparatus may comprise glass or plastic channels incorporated into microchip analyzers. Albeit the sample path will usually be rectilinear, it will be appreciated that the elongate path referred to herein may (in appropriate circumstances) be curvilinear and of relatively complex, compound configuration as well. A fluidic device, used for sample introduction, and to push or pull the sample into the SER-active medium and to effect distribution thereupon or therewithin, can also take many different forms, it being appreciated that the functional features of the device may be important from the standpoint of assuring the intimacy of contact necessary for efficient separation of the analyte chemical(s).

Similarly, and as mentioned above, the optical device employed to irradiate the sample and collect SER radiation can take many different forms. In addition to the examples already given, however, such a device may desirably comprise a cylindrical lens that is effective to focus the excitation laser radiation in the shape of a line along the length of rectilinear containment means, and to collect the SER scattered radiation, such that it can be spread along one axis of a two-dimensional array detector, the other axis being used to obtain the Raman spectrum as a function of wavenumbers. An optical device comprising a cylindrical lens probe 38 is diagrammatically shown in FIG. 4 (as an alternative to the probe 30). It will be noted that the axis of the lens probe 38 (essentially that of the cylindrical lens) is parallel to that of the microchannel 24, and that its length corresponds to the length (essentially, of the lens) of the section 27 of the channel that contains the SER-active sol-gel medium. It will be appreciated that, in such an arrangement, the stage 36 would normally be disposed in a fixed axial relationship relative to the cylindrical lens of the probe 38, and that the optics would include means (e.g., a grating) for dispersing the spectra of Raman scattered radiation across a two-dimensional detector, one dimension representing the spectra and the other the irradiated length of the channel, to thereby enable analysis of the constituent spectral features.

Numerous applications can benefit from the method and apparatus of the invention, including, for example, the detection of chemical contaminants (e.g. $CN^-$, $CrO_4^-$) in groundwater, the determination of drug presence and efficacy (by analysis for a parent constituent and/or its metabolites in a biological fluid), and the detection of chemical agent hydrolysis products in poisoned water. Other applications will readily occur to those skilled in the art.

It should be understood that the term "solution" is used in a broad sense in the present description and claims. It is intended to encompass colloidal suspensions (of dispersed solid, semisolid, and liquid particles) in a fluid (gas or liquid) continuous phase, as well as true solutions (i.e., at the molecular or ionic level) of one or more dissolved substances in a simple or mixed fluid solvent.

Thus, it can be seen that the present invention provides a novel method and apparatus for the qualitative and quantitative analysis of chemicals in solution. More specifically, the invention provides such a method and apparatus by which at least one analyte chemical can be rapidly separated from a sample solution, and quickly detected for ultimate analysis.

Having thus described the invention, what is claimed is:

1. In apparatus for the analysis of a sample solution containing a plurality of chemicals, including at least one analyte chemical, effected with the rapid separation and subsequent detection of the at least the one analyte chemical, the combination of comprising:

a microchannel comprising a stationary medium and being sufficiently transparent to excitation radiation, at least at a plurality of locations, to permit transmission of excitation radiation effective for generating measurable amounts of surface-enhanced Raman scattered radiation, and being sufficiently transparent to such scattered Raman radiation, at least at said plurality of locations, to permit transmission of measurable amounts of such scattered Raman radiation;

a stationary medium contained in said microchannel and comprised of at least one separation material and at least one metal having surface-enhanced Raman scattering activity, said at least one metal being of particulate form, and that is functional to separate the at least one chemical contained in the sample solution and to exhibit surface-enhanced Raman scattering activity, said stationary medium comprising or defining an elongate path for the sample solution, and said plurality of locations being along said elongate path;

an entrance into said microchannel for introducing a sample solution at a location adjacent one end of said elongate path, said at least said plurality of locations being spaced from said entrance along said microchannel;

an exit adjacent the opposite end of said elongate path; and driving force-producing means, operatively connected to one of said entrance into said microchannel and said exit adjacent the opposite end of said elongate path, for promoting flow of the sample solution away for said location of introduction, and for effecting distribution of the sample through said stationary medium, along said elongate path.

2. The apparatus of claim 1 wherein said elongate path is rectilinear.

3. The apparatus of claim 1 wherein said at least one metal having surface-enhanced Raman scattering activity is selected from the group consisting of silver, gold, copper, and alloys and mixtures thereof.

4. The apparatus of claim 1 comprising a microchip card substrate bearing said microchannel.

5. The apparatus of claim 4 wherein said substrate has a port communicating with said entrance of said microchannel and has an excess sample chamber adjacent said opposite end of said elongate flow path and in fluid flow communication with said exit of said microchannel.

6. The apparatus of claim 4 additionally including Raman spectrometer means comprised of a stage for mounting said microchip card substrate, and an optical device for irradiating said stationary medium, contained in said microchannel on said microchip card substrate, when said substrate is mounted on said stage of said spectrometer means, and for collecting SER scattered radiation from said stationary medium.

7. The apparatus of claim 6 wherein said microchannel is elongate and rectilinear.

8. The apparatus of claim 7 wherein said Raman spectrometer means includes an optical device for irradiating said stationary medium in said microchannel and for collecting SER scattered radiation therefrom, said optical device being either a probe that is mounted for scanning, by relative movement, along the length of said stationary medium, or comprising a cylindrical lens having its axis aligned with said microchannel.

9. The apparatus of claim 1 wherein said stationary medium comprises a lining deposited on a wall of said microchannel and defining said elongate path.

10. The apparatus of claim 1 wherein the particles of said metal having surface-enhanced Raman scattering activity are of submicron size.

11. The apparatus of claim 1 wherein said metal having surface-enhanced Raman scattering activity comprises metal colloids or metal-coated particles of polystyrene, silica, alumina, zirconia or titania.

12. The apparatus of claim 11 wherein said metal having surface-enhanced Raman scattering activity comprises metal-coated particles in the form of spheres of submicron size.

13. The apparatus of claim 11 wherein said metal having surface-enhanced Raman scattering activity comprises particles that are substantially isolated from one another.

14. The apparatus of claim 11 wherein said metal having surface-enhanced Raman scattering activity is in the form of particulate groupings or elements of substantially regular character, to optimize surface-enhanced Raman scattering.

15. The apparatus of claim 1 wherein said stationary medium comprises a fixed surface deposit.

16. The apparatus of claim 1 wherein said at least one separation material is in the form of particles, matrices, gels, sol-gels, or integral elements.

17. The apparatus of claim 16 wherein said at least one separation material comprises an integral element in the form of a porous plug, or a fixed surface deposit.

18. The apparatus of claim 1 wherein said at least one separation material is of particulate form, wherein said particulate materials constitute a homogeneous mixture, and wherein said at least one separation material is present in said stationary medium in a volumetric ratio to said at least one metal having surface-enhanced Raman scattering activity in the range of about $1 \times 10^6:1$ to $1:10^2$.

19. The apparatus of claim 1 wherein said stationary medium comprises at least one separation material selected from the group consisting of aero-gels, zero-gels, metal alkoxide-based sol-gels, silica gels, transition metal-stabilized silica, derivatized silica-based matrices, glass beads, long-chain alkanes, derivatized long-chain alkanes, polymers, derivatized polymers, membranes, functionalized membranes, alumina, size-exclusion resins, and ion-exchange resins.

20. The apparatus of claim 1 wherein said stationary medium comprises a liquid chromatography separation material.

* * * * *